US010459073B2

(12) United States Patent
Oshima et al.

(10) Patent No.: US 10,459,073 B2
(45) Date of Patent: Oct. 29, 2019

(54) ACOUSTIC WAVE DIAGNOSTIC APPARATUS AND METHOD OF CONTROLLING SAME

(71) Applicant: FUJIFILM Corporation, Tokyo (JP)

(72) Inventors: Yuji Oshima, Ashigarakami-gun (JP); Yukiya Miyachi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 429 days.

(21) Appl. No.: 15/018,141

(22) Filed: Feb. 8, 2016

(65) Prior Publication Data
US 2016/0259040 A1 Sep. 8, 2016

(30) Foreign Application Priority Data
Mar. 5, 2015 (JP) ................. 2015-043588

(51) Int. Cl.
*G01S 7/56* (2006.01)
*G01S 15/89* (2006.01)
(Continued)

(52) U.S. Cl.
CPC ................ *G01S 7/56* (2013.01); *A61B 8/461* (2013.01); *A61B 8/488* (2013.01); *A61B 8/5207* (2013.01);
(Continued)

(58) Field of Classification Search
CPC ........ G01S 7/56; G01S 15/58; G01S 7/52053; G01S 15/8986; G01S 15/8979;
(Continued)

(56) References Cited

U.S. PATENT DOCUMENTS 6,106,462 A * 8/2000 Yaegashi ............. H03H 7/0115
600/437
7,968,851 B2 * 6/2011 Rousso ................... G01T 1/161
250/370.09
(Continued)

FOREIGN PATENT DOCUMENTS

JP  2007-29198 A    2/2007
JP  2008-191393 A   8/2008
JP  2011217842 A  * 11/2011

OTHER PUBLICATIONS

Extended European Search Report dated Jul. 15, 2016, for European Application No. 16156519.7.

*Primary Examiner* — Isam A Alsomiri
*Assistant Examiner* — Amie M Ndure
(74) *Attorney, Agent, or Firm* — Birch, Stewart, Kolasch & Birch, LLP

(57) ABSTRACT

If the boundary value of a velocity scale set in a case where the information indicating the velocity of the moving body is displayed on a liquid crystal panel is less than a threshold value, the frequency of pulses used in pulse-width control is set to 20 kHz in such a manner that noise ascribable to the pulses for pulse-width control will not be displayed on the liquid crystal panel. If the boundary value of the velocity scale is equal to or greater than the threshold value, then the frequency of pulses used in pulse-width control is set to 200 Hz in such a manner that noise ascribable to the pulses for pulse-width control will reside at a position remote from the information indicative of velocity.

10 Claims, 13 Drawing Sheets

(51) Int. Cl.
*G01S 7/52* (2006.01)
*A61B 8/00* (2006.01)
*A61B 8/08* (2006.01)
*G01S 15/58* (2006.01)

(52) U.S. Cl.
CPC .......... *A61B 8/546* (2013.01); *G01S 7/52053* (2013.01); *G01S 7/52077* (2013.01); *G01S 7/52096* (2013.01); *G01S 15/58* (2013.01); *G01S 15/8979* (2013.01); *G01S 15/8988* (2013.01); *G01S 7/52079* (2013.01); *G01S 15/8986* (2013.01)

(58) Field of Classification Search
CPC ............. G01S 7/52077; G01S 15/8988; G01S 7/52096; G01S 7/52079; A61B 8/00; A61B 8/08; A61B 8/461; A61B 8/488; A61B 8/5207; A61B 8/546
See application file for complete search history.

(56) References Cited

U.S. PATENT DOCUMENTS

| | | | | |
|---|---|---|---|---|
| 8,000,773 B2 * | 8/2011 | Rousso | ................. | A61B 5/415 250/370.08 |
| 8,088,071 B2 * | 1/2012 | Hwang | ................. | G01S 7/52079 600/437 |
| 8,506,491 B2 * | 8/2013 | Wu | ................. | A61B 8/4427 327/145 |
| 8,571,881 B2 * | 10/2013 | Rousso | ................. | A61B 5/417 600/431 |
| 8,606,349 B2 * | 12/2013 | Rousso | ................. | A61B 5/418 424/9.1 |
| D699,359 S * | 2/2014 | Lindekugel | ................. | D24/186 |
| 8,644,910 B2 * | 2/2014 | Rousso | ................. | A61B 5/02755 250/370.09 |
| 9,091,740 B2 * | 7/2015 | Kwon | ................. | H04W 56/00 |
| 2003/0013966 A1 * | 1/2003 | Barnes | ................. | A61B 5/0402 600/446 |
| 2006/0094960 A1 * | 5/2006 | Phung | ................. | G01S 7/52017 600/437 |
| 2007/0167770 A1 * | 7/2007 | Miyaki | ................. | A61B 8/06 600/437 |
| 2009/0018442 A1 * | 1/2009 | Miller | ................. | G01S 7/52077 600/437 |
| 2009/0163816 A1 * | 6/2009 | Azuma | ................. | A61B 8/06 600/454 |
| 2011/0230767 A1 * | 9/2011 | Miyajima | ................. | A61B 8/00 600/459 |

\* cited by examiner

ACOUSTIC WAVE DIAGNOSTIC APPARATUS AND METHOD OF CONTROLLING SAME

CROSS-REFERENCE TO RELATED APPLICATIONS

The present application claims priority under 35 U.S.C. § 119 to Japanese Patent Application No. 2015-043588 filed Mar. 5, 2015. Each of the above application(s) is hereby expressly incorporated by reference, in its entirety, into the present application.

BACKGROUND OF THE INVENTION

Field of the Invention

This invention relates to an acoustic wave diagnostic apparatus and to a method of controlling such apparatus.

Description of the Related Art

With an ultrasound diagnostic apparatus, a tomographic image of a specimen is obtained by transmitting ultrasound waves toward the specimen and making use of an ultrasound echo signal that represents an ultrasound echo from the specimen. With a pulsed-Doppler ultrasound diagnostic apparatus that employs a resonating-type switching power supply, there is the danger of misdiagnosis owing to the mixing of noise with a blood flowrate pattern, which is displayed on a screen, due to the switching frequency and resonant frequency. For this reason, there are instances where control is exercised in such a manner that whole-number multiples of the switching frequency and resonant frequency of the power supply fall outside the shift region of the Doppler shift frequency (Prior Art Document 1). Further, there is an arrangement in which pulse-width control is utilized in backlighting in an ultrasound diagnostic apparatus (Prior Art Document 2).

Patent Document 1: Japanese Patent Application Laid-Open No. 2007-29198

Patent Document 2: Japanese Patent Application Laid-Open No. 2008-191393

FIGS. 16 and 17 are examples of a display screen of an ultrasound diagnostic apparatus for measuring the velocity of a blood flow or the like. The velocity scale in both FIGS. 16 and 17 is represented by Doppler shift frequency. Since there is a fixed relationship between velocity and Doppler shift frequency, there are also cases where the velocity scale is represented by velocity as well as cases where it is represented by frequency. FIG. 16 illustrates noise 120, which is produced on a display screen 60 when the pulse frequency used in pulse-width control is 200 Hz, in a case where the boundary value of a velocity scale 120A to be set has been set to 2.3 kHz and, moreover, backlighting of the display device is controlled using pulse-width control. The six waveforms extending along the horizontal direction are noise. Thus, the noise 120, which has a frequency that is a whole-number multiple of 200 Hz utilized as the pulse frequency, is produced. FIG. 17 illustrates noise 121 produced on the display screen 60 in a case where the boundary value of the velocity scale 120A to be set has been set to 41.7 kHz and the pulse frequency used in pulse-width control is 20 kHz. Thus, when backlighting of the display device is controlled utilizing pulse-width control, noise 120 or 121 appears on the display screen 60 and this can bring about misdiagnosis. Whereas the Doppler shift frequency used in diagnosis generally is on the order of 100 Hz to 50 kHz, the frequency of pulses used in backlight control is on the order of 200 to 20 kHz. Since both frequencies happen to overlap, the above-mentioned noise appears on the display screen. In particular, since a high sensitivity is required in a continuous-wave Doppler ultrasound diagnostic apparatus used to detect weak-power backflow, noise is even more conspicuous. In both Prior Art Documents 1 and 2, absolutely no consideration is given to elimination of the effects of noise thus produced by pulse-width control.

SUMMARY OF THE INVENTION

An object of the present invention is to eliminate the effects of noise produced by pulse-width control.

An acoustic wave diagnostic apparatus according to a first aspect of the present invention comprises: an acoustic probe for transmitting acoustic waves (not only ultrasound waves but including also sound waves in the audible region) toward a specimen and outputting an acoustic echo signal representing an acoustic echo from the specimen; a velocity scale setting device (velocity scale setting means) for setting a velocity scale; a velocity calculation device (velocity calculation means) for calculating velocity of a moving body (not only a fluid such as blood but including also a moving target such as the wall of the heart) within the specimen using the acoustic echo signal output from the acoustic probe; a display control device (display control means) for displaying information, which indicates velocity calculated by the velocity calculation device, on a display unit in accordance with the velocity scale set by the velocity scale setting device; a brightness control device (brightness control means) for controlling brightness of the display unit (based upon pulse width); and a frequency setting device (frequency setting means) for setting the frequency of pulses used in the brightness control device to a first frequency (where the first frequency is, for example, a frequency equal to or greater than a frequency corresponding to a first boundary value) in a case where a velocity scale that includes the first boundary value, which is less than a threshold value, has been set (the setting of the first boundary value) by the velocity scale setting device, and setting the frequency of pulses used in the brightness control device to a second frequency (where the second frequency is, for example, a frequency less than a frequency corresponding to the first boundary value) lower than the first frequency in a case where a velocity scale that includes a second boundary value, which is equal to or greater than the threshold value, has been set by the velocity scale setting device.

The first aspect of the present invention provides also a method of controlling an acoustic wave diagnostic apparatus. Specifically, the first aspect of the present invention comprises steps of: an acoustic probe transmitting acoustic waves toward a specimen and outputting an acoustic echo signal representing an acoustic echo from the specimen; a velocity scale setting device setting a velocity scale; a velocity calculation device calculating velocity of a moving body within the specimen using the acoustic echo signal output from the acoustic probe; a display control device displaying information, which indicates velocity calculated by the velocity calculation device, on a display unit in accordance with the velocity scale set by the velocity scale setting device; a brightness control device controlling brightness of the display unit (based upon pulse width); and a frequency setting device setting the frequency of pulses used in the brightness control device to a first frequency in a case where a velocity scale that includes a first boundary value, which is less than a threshold value, has been set by the velocity setting device, and setting the frequency of pulses used in the brightness control device to a second frequency lower than the first frequency in a case where a velocity scale that includes a second boundary value, which is equal to or greater than the threshold value, has been set by the velocity scale setting device.

An acoustic wave diagnostic apparatus according to a second aspect of the present invention comprises: an acoustic probe for transmitting acoustic waves toward a specimen and outputting an acoustic echo signal representing an acoustic echo from the specimen; a velocity scale setting device (velocity scale setting means) for setting a velocity scale; a velocity calculation device (velocity calculation means) for calculating velocity of a moving body (not only a fluid such as blood but including also a moving target such as the wall of the heart) within the specimen using the acoustic echo signal output from the acoustic probe; a display control device (display control means) for displaying information, which indicates velocity calculated by the velocity calculation device, on a display unit in accordance with the velocity scale set by the velocity scale setting device; a cooling fan for cooling at least one of the velocity calculation device and display control device; a fan motor for controlling rotation of the cooling fan (based upon pulse width); and a frequency setting device (frequency setting means) for setting the frequency of pulses used in the fan motor to a first frequency (where the first frequency is, for example, a frequency equal to or greater than a frequency corresponding to a first boundary value) in a case where a velocity scale that includes the first boundary value, which is less than a threshold value, has been set by the velocity scale setting device, and setting the frequency of pulses used in the fan motor to a second frequency (where the second frequency is, for example, a frequency less than a frequency corresponding to the first boundary value) lower than the first frequency in a case where a velocity scale that includes a second boundary value, which is equal to or greater than the threshold value, has been set by the velocity scale setting device.

The second aspect of the present invention provides also a method of controlling an acoustic wave diagnostic apparatus. Specifically, the second aspect of the present invention comprises steps of: an acoustic probe transmitting acoustic waves toward a specimen and outputting an acoustic echo signal representing an acoustic echo from the specimen; a velocity scale setting device setting a velocity scale; a velocity calculation device calculating velocity of a moving body within the specimen using the acoustic echo signal output from the acoustic probe; a display control device displaying information, which indicates velocity calculated by the velocity calculation device, on a display unit in accordance with the velocity scale set by the velocity scale setting device; a cooling fan cooling at least one of the velocity calculation device and display control device; a fan motor controlling rotation of the cooling fan (based upon pulse width); and a frequency setting device setting the frequency of pulses used in the fan motor to a first frequency in a case where a velocity scale that includes a first boundary value, which is less than a threshold value, has been set, and setting the frequency of pulses used in the fan motor to a second frequency lower than the first frequency in a case where a velocity scale that includes a second boundary value, which is equal to or greater than the threshold value, has been set by the velocity scale setting device.

The apparatus may further comprise a high-pass filter (high-pass filter means), which has a cut-off frequency equal to or greater than the second frequency, for eliminating low-frequency components of the acoustic echo signal that is output from the acoustic probe.

Preferably, duty ratio of pulses at the first frequency and duty ratio of pulses at the second frequency are identical.

By way of example, the acoustic wave diagnostic apparatus is such that the acoustic probe transmits continuous waves of acoustic waves, and the display control device displays a waveform, which indicates the velocity of a moving body within the specimen, on the display unit.

The apparatus may further comprise a low-pass filter (low-pass filter means) for eliminating high-frequency components, at a cut-off frequency equal to or greater than the frequency corresponding to the velocity of the first boundary value, from the acoustic echo signal that is output from the acoustic probe, in a case where a velocity scale that includes the first boundary value has been set by the velocity scale setting device.

By way of example, the acoustic wave diagnostic apparatus transmits is such that the acoustic probe transmits pulsed acoustic waves at regular intervals, and the display control device displays a waveform, which indicates the velocity of a moving body within the specimen, on the display unit.

By way of example, the acoustic wave diagnostic apparatus is such that the acoustic probe transmits pulsed acoustic waves from the acoustic probe at regular intervals, and the display control device is a color Doppler display control device (color Doppler display control means) for displaying information, which represents the velocity a moving body within the specimen as a difference in color, on the display unit.

In accordance with the first aspect of the present invention, the frequency of pulses used in the brightness control device is set to a first frequency in a case where a velocity scale that includes a first boundary value less than a threshold value has been set, and the frequency of pulses used in the brightness control device is set to a second frequency lower than the first frequency in a case where a velocity scale that includes a second boundary value equal to or greater than the threshold value has been set. Since the frequency corresponding to the first boundary value that is less than the threshold value is comparatively low, a comparatively high first frequency is set to the frequency of pulses used in the brightness control device. Since noise ascribable to pulses (to pulse-width control thereof) having the first frequency is a comparatively high frequency, there is a high probability that the noise will fall outside the range of the velocity scale that includes the first boundary value and, hence, the noise will no longer be displayed on the display screen. On the other hand, since the frequency corresponding to the second boundary value that is equal to or greater than the threshold value is comparatively high, a comparatively low second frequency is set to the frequency of pulses used in the brightness control device. Since noise ascribable to pulses (to pulse-width control thereof) having the second frequency is a comparatively low frequency, the noise will merely appear at the lower portion of the velocity scale that includes the second boundary value and will not be conspicuous. The influence upon ultrasound diagnosis of noise ascribable to pulse (width) control can be eliminated.

In the second aspect of the present invention as well, the frequency of pulses used in the fan motor is set to a first frequency in a case where a velocity scale that includes a first boundary value less than a threshold value has been set, and the frequency of pulses used in the fan motor is set to a second frequency lower than the first frequency in a case where a velocity scale that includes a second boundary value equal to or greater than the threshold value has been set. Since the frequency corresponding to the first boundary value that is less than the threshold value is comparatively low, a comparatively high first frequency is set to the frequency of pulses used in the fan motor. Since noise ascribable to pulses (to pulse-width control thereof) having the first frequency is a comparatively high frequency, there is a high probability that the noise will fall outside the range of the velocity scale that includes the first boundary value and, hence, the noise will no longer be displayed on the display screen. On the other hand, since the frequency corresponding to the second boundary value that is equal to or greater than the threshold value is comparatively high, a comparatively low second frequency is set to the frequency of pulses used in the fan motor. Since noise ascribable to pulses (to pulse-width control thereof) having the second frequency is a comparatively low frequency, the noise will merely appear at the lower portion of the velocity scale that includes the second boundary value and will not be conspicuous. The influence upon ultrasound diagnosis of noise ascribable to pulse (width) control can be eliminated.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Figure 1:
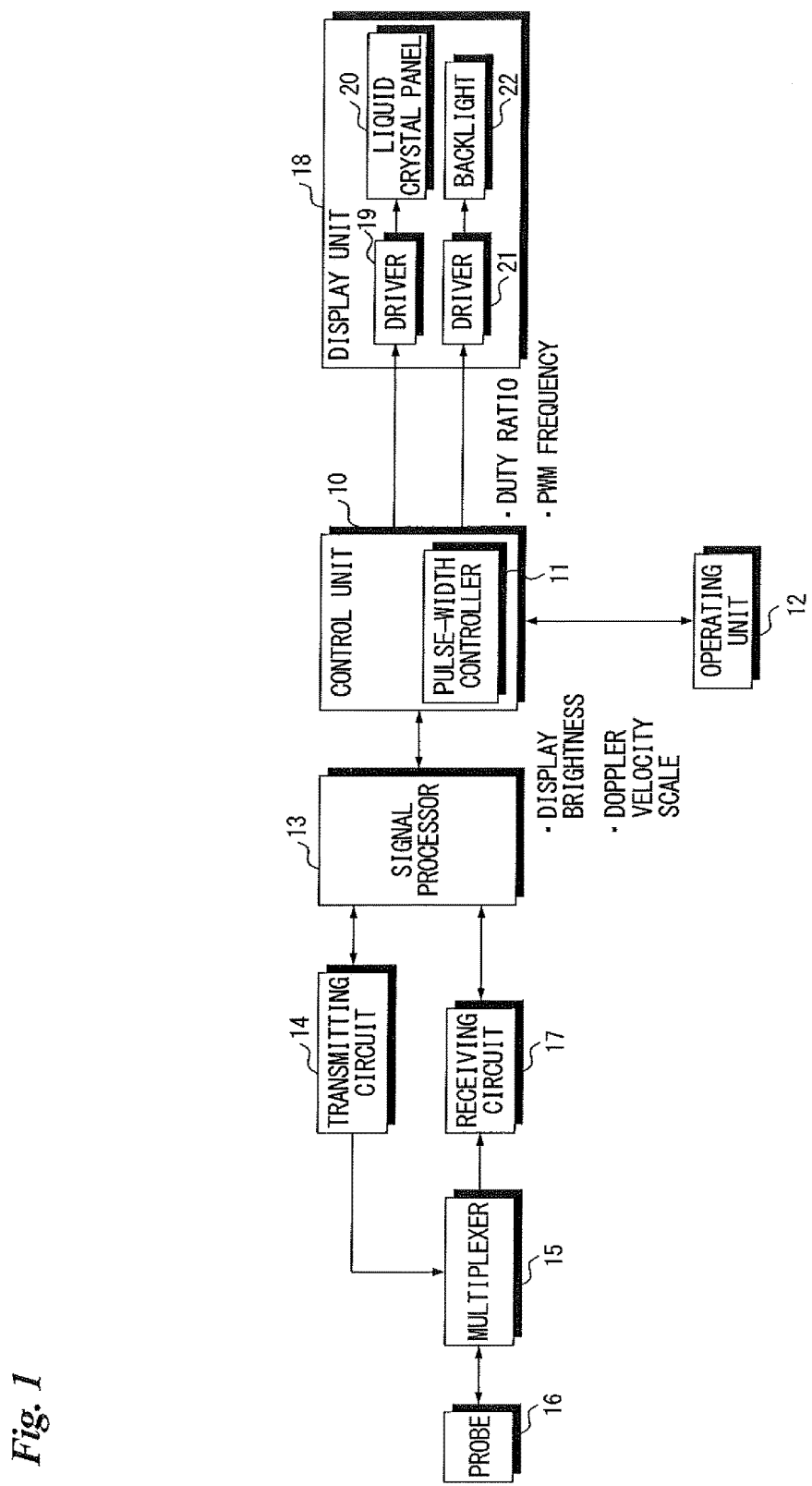
FIG. 1 is a block diagram illustrating the electrical configuration of an ultrasound diagnostic apparatus.

FIG. 1 is a block diagram illustrating the electrical configuration of an ultrasound diagnostic apparatus (acoustic wave diagnostic apparatus).

In this embodiment, ultrasound waves are used as the acoustic waves but the invention is not limited to ultrasound waves and it may be so arranged that acoustic waves of audible frequencies are used if an appropriate frequency is selected in accordance with the specimen (object under examination) or diagnostic conditions or the like. Further, the embodiment is not only utilized in the diagnosing of illness of a human being as the specimen but can also be utilized in a case where a moving body such as water flowing through piping or the like is investigated by generating an acoustic image (ultrasound image).

The overall operation of the ultrasound diagnostic apparatus is controlled by a control unit 10.

The ultrasound diagnostic apparatus includes a display unit 18. The display unit 18 includes a liquid crystal panel 20 on the display screen of which is displayed information (graphs and colors and the like indicating velocity) indicating the velocity of a moving body (a fluid such as blood in the specimen or a moving body such as the wall of the heart). The brightness of the liquid crystal panel 20 is adjusted by a backlight 22.

The user (a person such as a physician, nurse or technician) of the ultrasound diagnostic apparatus sets the brightness and Doppler velocity scale of the display unit 18 (backlight 22) using an operating unit 12 (velocity scale setting device for setting a velocity scale). The Doppler velocity scale is a scale that indicates the range of display of information indicative of velocity of the moving body displayed on the liquid crystal panel 20. Signals indicating the set brightness and Doppler velocity scale are applied to the control unit 10. In the embodiment described in this specification, the control unit 10 possesses a pulse-width controller 11 (a pulse-width control function) as well as a display control device (display control function) described later. However, this is not a limiting condition and the control function and pulse-width controller 11 may just as well be provided separately. Pulses of a frequency having a duty ratio corresponding to the set brightness are generated by the pulse-width control function (a brightness control device or brightness control means for controlling the brightness of the display unit based upon pulse width), and the pulses are applied to a driver 21. The backlight 22 is driven by the driver 21 and the liquid crystal panel 20 is illuminated by the light from the backlight 22. In this embodiment, as will be described later in detail, the frequency of the pulses utilized in pulse-width control is changed in accordance with the Doppler scale that has been set. Changing the frequency of the pulses prevents or renders inconspicuous the appearance of noise, which is ascribable to the frequency of the pulses utilized in pulse-width control, on the liquid crystal panel 20.

The control unit 10 outputs a control signal for the purpose of transmitting ultrasound waves to the specimen and applies this control signal to a transmitting circuit 14 via a signal processor 13. A control signal from the transmitting circuit 14 is applied to an ultrasound probe 16 via a multiplexer 15. Ultrasound waves are transmitted from an ultrasonic vibrator included in the ultrasound probe 16 and propagate through the interior of the specimen. An ultrasound echo from within the specimen is received by the ultrasonic vibrator inside the ultrasound probe 16 and is converted to an ultrasound echo signal in the ultrasonic vibrator. The ultrasound echo signal obtained by the conversion is output from the ultrasound probe 16 and is input to a receiving circuit 17 via the multiplexer 15.

Figure 2:
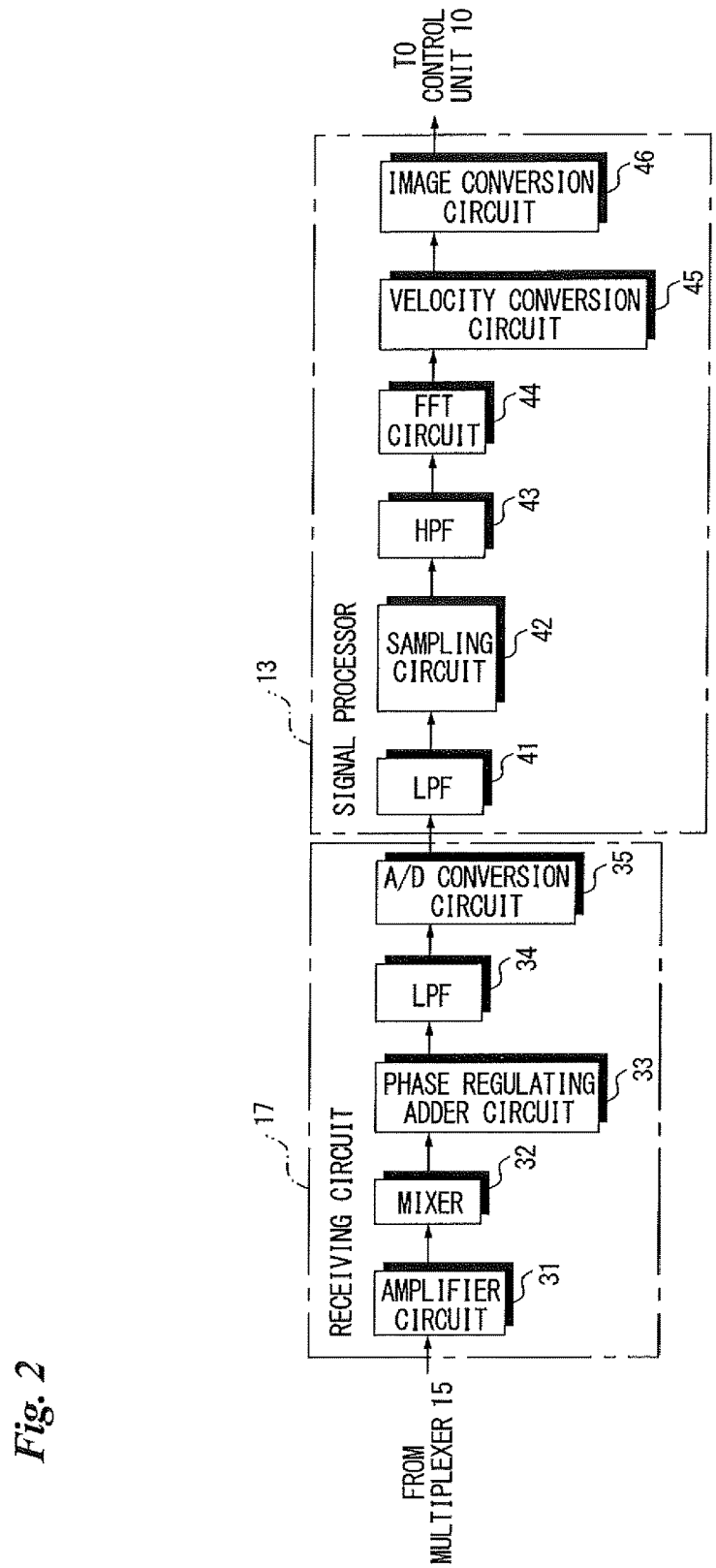
FIG. 2 is a block diagram illustrating the electrical configurations of a signal processor and receiving circuit.

FIG. 2 is a block diagram illustrating the electrical configurations of portions of the receiving circuit 17 and signal processor 13. The block diagram illustrated in FIG. 2 is an apparatus (a so-called continuous-wave Doppler ultrasound diagnostic apparatus) in which the ultrasound diagnostic apparatus shown in FIG. 1 transmits continuous waves of ultrasound from the ultrasound probe 16 and displays a waveform, which indicates the velocity of the moving body, on the liquid crystal panel (display unit) 20.

The ultrasound echo signal that has been input to the receiving circuit is amplified in an amplifier circuit 31 and detected by a mixer 32, whereby the signal is converted to a baseband signal. The output signal from the mixer 32 is applied to a phase regulating adder circuit 33 where the signal undergoes phase-regulated addition with an ultrasound echo signal that is output from a different ultrasonic vibrator included in the ultrasound probe 16. The output signal from the phase regulating adder circuit 33 is input to an LPF (low-pass filler) 34. The latter is a filter for performing anti-aliasing prior to an analog-to-digital conversion. The output signal of the low-pass filter 34 is converted to digital ultrasound echo data in an A/D (analog-to-digital) conversion circuit 34, and the data is output from the receiving circuit 17.

The signal processor 13 functions to process the ultrasound echo data accepted from the receiving circuit 17 and to calculate the velocity of the moving body within the specimen. The ultrasound echo data output from the receiving circuit 17 is input to a low-pass filter 41 in the signal processor 13. The low-pass filter 41 has a cut-off frequency on the order of a Doppler shift frequency that corresponds to a boundary value (a first boundary value, described later) of the Doppler velocity scale that has been set by the operating unit 12. As will be described later, aliasing noise produced in the liquid crystal panel 20 is removed by the low-pass filter 41. The output signal from the low-pass filter 41 is input to a sampling circuit 42, which performs sampling at a sampling frequency that is twice the boundary value of the Doppler shift frequency. The signal output from the sampling circuit 42 is applied to an HPF (high-pass filter) 43, which removes low-frequency components that are on the order of ⅒ to ½₀ of the boundary value (first boundary value, described later) of the Doppler shift frequency. (The HPF 43 is a high-pass filter having a cut-off frequency equal to or greater than a second frequency and removes low-frequency components from the acoustic echo signal that is output from the ultrasound probe 16). The cut-off frequency of the high-pass filter 43 may be ⅕ of the frequency (41.7 kHz) of a second boundary value, or lower. The output signal from the high-pass filter 43 is subjected to a high-speed Fourier transform in an FFT (fast-Fourier transform) circuit 44. The signal output from the fast-Fourier transform circuit 44 is converted to velocity in a velocity conversion circuit 45 (a velocity calculation device for calculating the velocity of the moving body within the specimen using the ultrasound echo signal obtained from the ultrasound probe 16). Velocity v of the moving body under measurement is obtained as velocity $v=(c/2)\times(fd/fs)$, where v represents the velocity v of the moving body to be measured, c the speed of sound (approximately 1530 m/s) within the specimen, fd the Doppler shift frequency and fs the detected frequency (about 1 to 10 MHz). The signal output from the velocity conversion circuit 45 is input to an image conversion circuit 46 where it is converted to a luminance commensurate with the power of the moving body. The output signal from the image conversion circuit 46 is the output signal of the signal processor 13 and is input to the control unit 10.

A driver 19 in the display unit 18 is controlled by the control unit (display control device) 10 and a waveform indicating the velocity of the moving body within the specimen is displayed on the liquid crystal panel (display unit) 20 in accordance with the velocity scale (see FIGS. 5 to 8, etc.).

The ultrasound diagnostic apparatus according to this embodiment is such that, in a case where a velocity scale that includes a first boundary value, which is less than a threshold value, has been set by the operating unit 12 (velocity scale setting device), the frequency of pulses used for the pulses of pulse-width control for controlling the brightness of the backlight 22 is set by the control unit 10 (pulse-width controller 11) to a first frequency (preferably a frequency higher than a frequency corresponding to the first boundary value), and in a case where a velocity scale that includes a second boundary value equal to or greater than the threshold value has been set by the operating unit 12, the frequency of pulses used for the pulses of pulse-width control for controlling the brightness of the backlight 22 is set by the control unit 10 (pulse-width controller 11) to a second frequency lower than the first frequency. Specifically, and by way of example, the threshold value is 18 kHz, the first boundary value is 2.3 kHz, the first frequency is 20 kHz, the second boundary value is 41.7 kHz and the second frequency is 200 Hz. It goes without saying that values other than these are permissible. Further, the first frequency may be a frequency equal to or greater than the frequency of the first boundary value and may be a frequency that is 0.9 to 1.1 times the frequency of the first boundary value.

Figure 3:
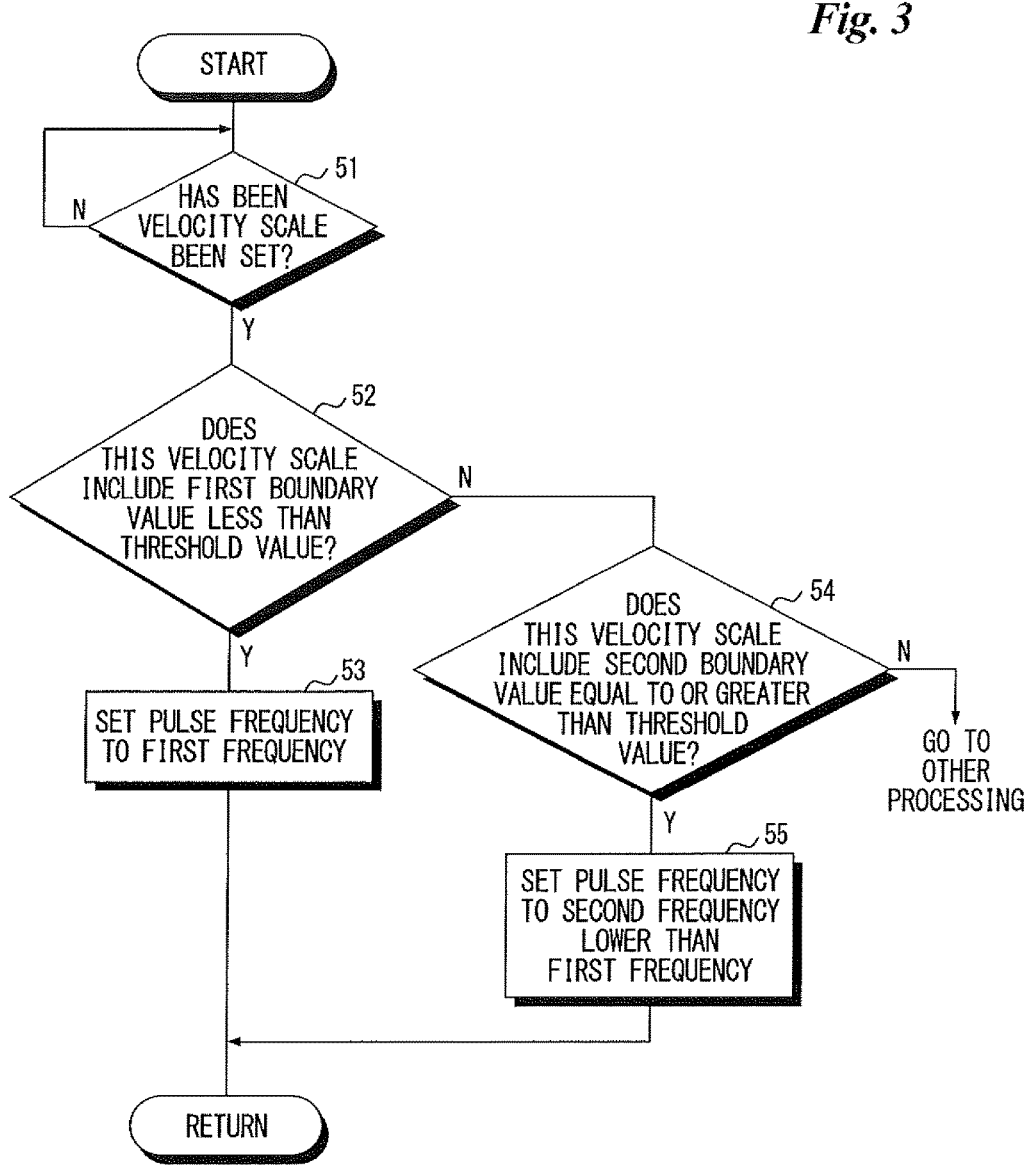
FIG. 3 is a flowchart illustrating the procedure of switching control of pulse frequency utilized in pulse-width control.
Figure 4:
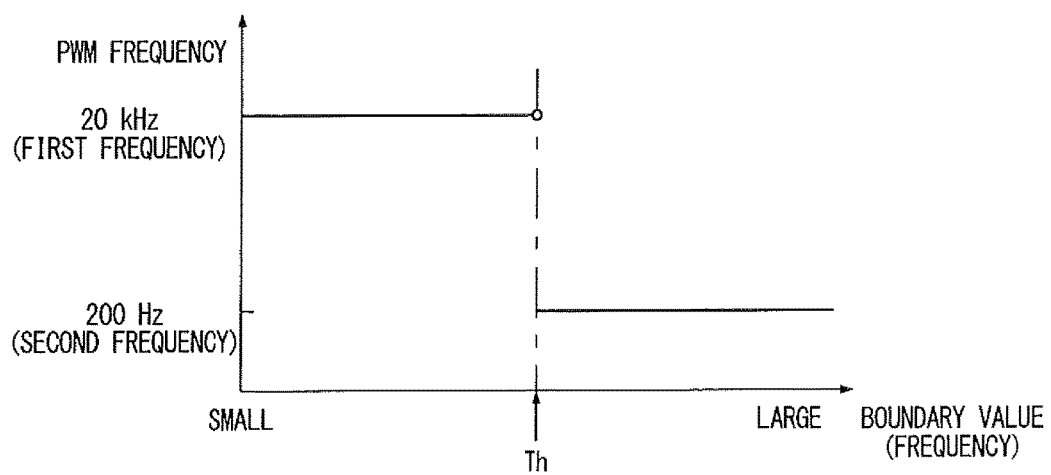
FIG. 4 illustrates the relationship between velocity-scale boundary values and pulse width.

FIG. 3 is a flowchart illustrating processing for setting the frequency of pulses used in pulse-width control, and FIG. 4 illustrates the relationship between boundary values of a velocity scale to be set and the frequency of pulses set in accordance with the boundary values.

With reference to FIG. 3, when the velocity scale is set by the user using the operating unit 12 (step 51), the control unit 10 determines whether the set velocity scale is one that includes the first boundary value, which is less than the threshold value (step 52). If the set velocity scale is one that includes the first boundary value that is less than the threshold value ("YES" at step 52), then the pulse frequency is set to the first frequency (step 53). With reference to FIG. 4, the threshold value is stipulated to be 18 kHz, as mentioned above. If a velocity scale that includes the first boundary value that is less than the threshold value is set, then the frequency of the pulses used in pulse-width control is set to 20 kHz, which is the first frequency.

If the set velocity scale is one that includes the second boundary value, which is equal to or greater than the threshold value ("NO" at step 52, "YES" at step 54), the pulse frequency is set to the second frequency (step 55). If the velocity scale that includes the second boundary value equal to or greater than the threshold value is set, the frequency of the pulses used in pulse-width control is set to 200 Hz, which is the second frequency, as shown in FIG. 4.

FIGS. 5 to 8 are examples of waveforms (waveforms of the velocity of a moving body, which is the target of measurement within the specimen) displayed on the liquid crystal panel 20.

Figure 5:
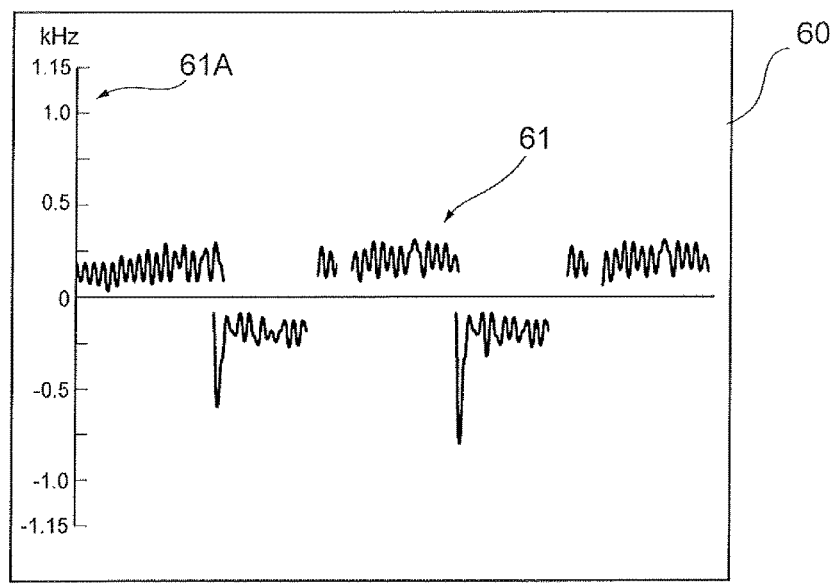
FIGS. 5 to 8 are examples of display screens of an ultrasound diagnostic apparatus.

FIG. 5 is an example of a display screen 60 in a case where a boundary value has been set to 2.3 kHz, which is the first boundary value.

The scale being displayed vertically on the left side of the display screen 60 shown in FIG. 5 is a velocity scale 61A. Here the velocity scale 61A is represented by a Doppler shift frequency. Doppler shift frequency and velocity are uniquely decided as will be understood from the equation set forth above. Therefore, the velocity scale 61A may just as well be represented as velocity rather than Doppler shift frequency. The same holds true with regard also to the velocity scales displayed on the other screens. A waveform 61 representing the velocity of a moving body is being displayed in accordance with the velocity scale 61A.

When a boundary value is set by the user in the ultrasound diagnostic apparatus of this embodiment, a velocity scale the upper and lower limits of which are values that are half this set boundary value is displayed on the display screen. In FIG. 5, for example, since the boundary value has been set to 2.3 kHz, the velocity scale 61A displayed is such that 1.15 kHz, which is half this boundary value of 2.3 kHz, is the upper limit of the velocity scale 61A, and −1.15 kHz is the lower limit of the velocity scale 61A. The reason for this is that, in this embodiment, the velocity scale 61A can be moved up and down, such movement allowing the portion of the velocity scale that is not being displayed on the display screen 60 before movement of the velocity scale 61A to be brought into view on the display screen. For example, with the velocity scale 61A being displayed such that 0 kHz, which is the reference point of the velocity scale 61A, is positioned substantially at the center along the vertical, as shown in FIG. 5, the display screen 60 will become as shown in FIG. 6 if the velocity scale 61A is moved downward by a command supplied from the operating unit 12.

Figure 6:
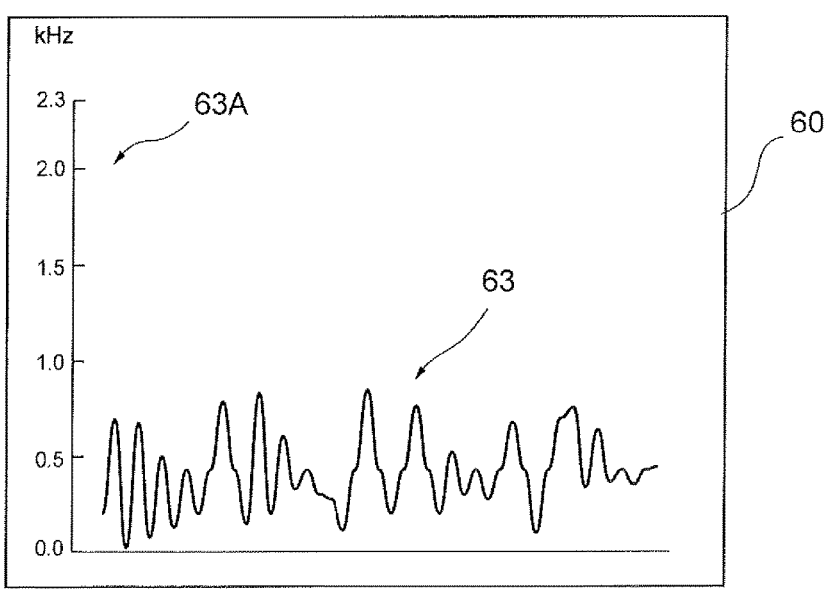

A velocity scale 63A is being displayed on the left side of the display screen 60 in FIG. 6. The upper limit of the velocity scale 63A is 2.3 kHz, which is the boundary value set by the user. Thus, movement of the velocity scale is possible. Therefore, in a case where 0 kHz serving as the reference point of the velocity scale 61A is displayed positioned at the center of the display screen 60, as shown in FIG. 5, a velocity scale in which values that are half the boundary value set by the user become the upper and lower limits is displayed on the display screen 60. Operation is similar for a case where the velocity scale 61A is moved upward as well.

For the reasons set forth above, when the user sets 2.3 kHz as the boundary value, the velocity scale 61A whose upper and lower limits are values that are half the boundary value is displayed on the display screen 60, as shown in FIG. 6. Since the set boundary value of 2.3 kHz is less than the threshold value (18 kHz), the pulse frequency used in pulse-width control of the backlight 22 is set to 20 kHz, as mentioned above. Since only a waveform that corresponds to the Doppler shift frequency of −1.15 to 1.15 kHz is displayed, noise produced from the pulse frequency of 20 kHz is not displayed. Since the waveform 61 representing the velocity of the moving body within the specimen is displayed but not noise ascribable to the pulses utilized in pulse-width control, misdiagnosis due to noise is prevented.

Further, since noise produced from the pulse frequency of 20 kHz is not displayed on the display screen 60 even in a case where the velocity scale 63A is moved downward (and similarly, even if it is moved upward), as shown in FIG. 6, only a waveform 63 representing the velocity of the moving body is displayed on the display screen 60. Misdiagnosis due to noise is prevented in this case as well.

Furthermore, the low-pass filter 41 is included in the signal processor 13. High-frequency components of the acoustic echo signal are removed by the low-pass filter 41 in which the boundary value (the first boundary value) is adopted as the cut-off frequency (which may be a frequency on the order of 10% of the frequency of the first boundary value). There are instances where the greater the extent to which noise components are not displayed on the display screen 60, the more aliasing noise appears even if the signal had high-frequency components. In this embodiment, even such aliasing noise is removed by the low-pass filter 41. As a result, aliasing noise is prevented from being displayed on the display screen 60.

Figure 7:
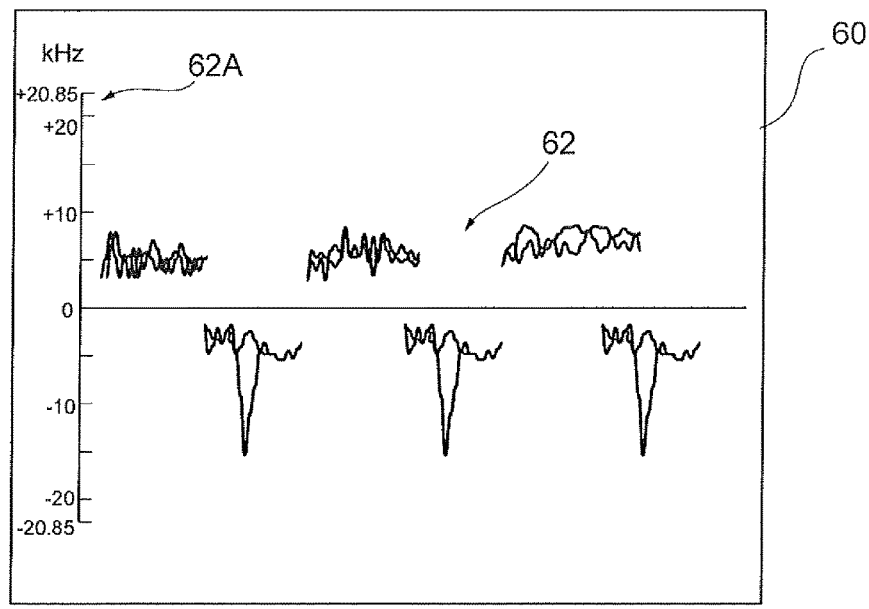

FIG. 7 is an example of the display screen 60 in a case where the boundary value has been set to 41.7 kHz, which is the second boundary value.

The scale being displayed vertically on the left side of the display screen 60 shown in FIG. 7 is a velocity scale 62A. As set forth above, 20.85 kHz, which is half the set boundary value of 41.7 kHz, is the upper limit of the velocity scale 62A, and −20.85 kHz is the lower limit of the velocity scale 62A. If the velocity scale 62A is moved downward in a manner similar to that described above, a velocity scale 64A whose set boundary value of 41.7 kHz is the upper limit is displayed on the display screen 60, as illustrated in FIG. 8.

Since the boundary value of 41.7 kHz set by the user is equal to or greater than the threshold value, the pulse frequency used in pulse-width control of the backlight 22 is set to 200 kHz, as mentioned above. The velocity scale being displayed on the display screen 60 is between −20.85 kHz and 20.85 kHz and has been set in such a manner that a waveform having a broad range of frequencies can be displayed. Since noise produced from the pulse frequency of 200 Hz can be considered to be substantially zero, noise has no influence upon waveform 62 (noise will not be conspicuous even if it appears on the display screen 60).

Figure 8:
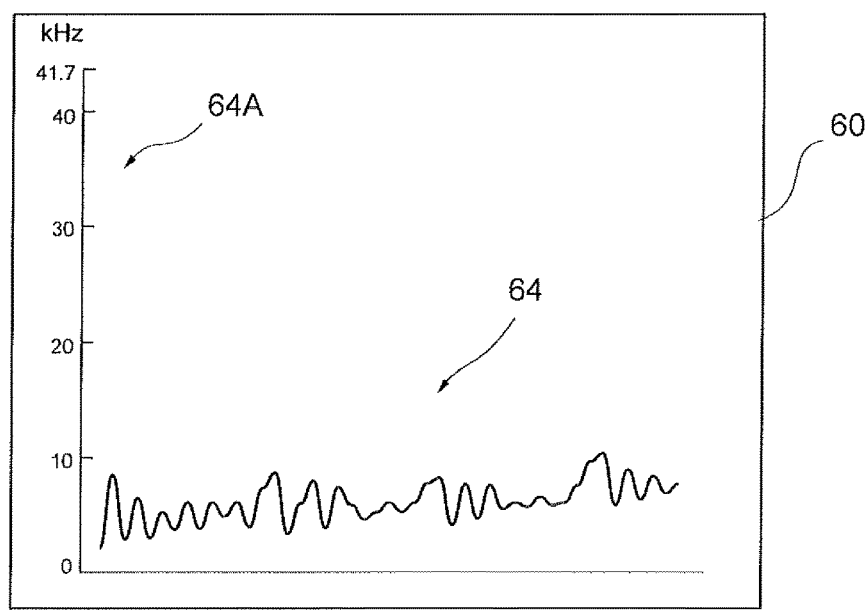

Further, even in a case where the velocity scale 62A is moved downward and the velocity scale 64A of 0 to 41.7 kHz is displayed, as shown in FIG. 8, noise produced from the pulse frequency of 200 Hz can be considered to be substantially zero and therefore noise has no influence upon the waveform (noise will not be conspicuous even if it appears on the display screen 60).

Furthermore, since low-frequency components are removed by the high-pass filter 43 (see FIG. 2) included in the signal processor 13, noise produced from the pulse frequency of 200 Hz is eliminated as well.

Figure 9:
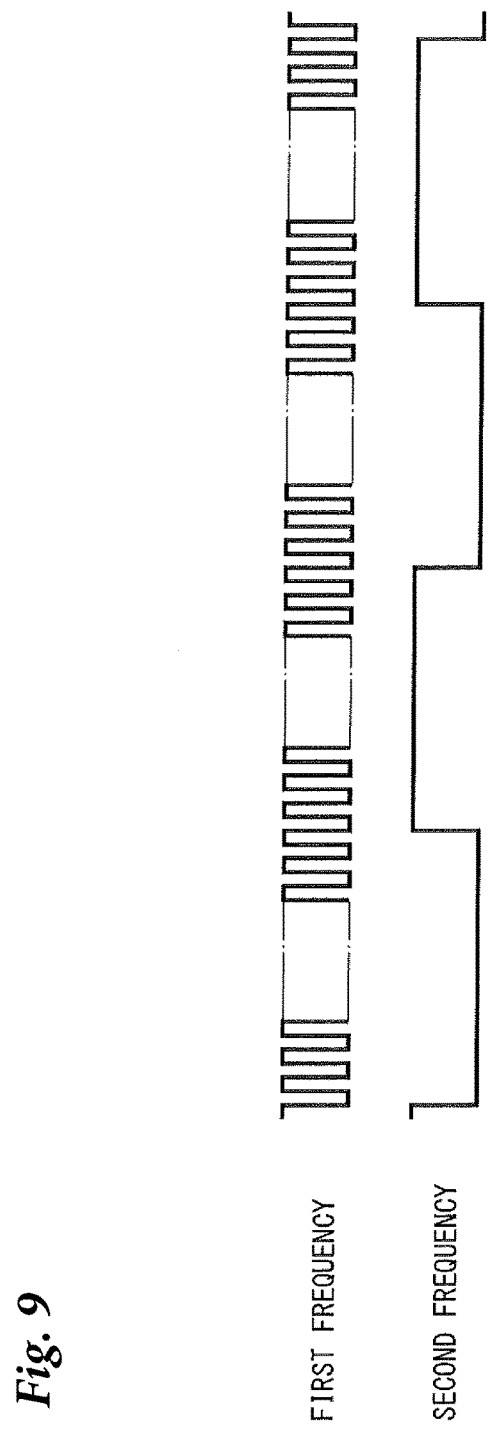
FIG. 9 illustrates pulses of a first frequency and pulses of a second frequency utilized in pulse-width control.

FIG. 9, which is an example of pulses used in pulse-width control, illustrates pulses of the first frequency and pulses of the second frequency.

The first frequency is 20 kHz and the second frequency is 200 Hz, as mentioned above.

In this embodiment, the duty ratio of the pulses having the first frequency and the duty ratio of the pulses having the second frequency are assumed to be substantially identical. The duty ratios are assumed to be substantially identical even if the difference between them is on the order of ±5%. In this embodiment, since the duty ratio of the pulses having the first frequency and the duty ratio of the pulses having the second frequency are substantially identical, the brightness of the backlight 22 will not change even if the frequency of the pulses used in pulse-width control is changed over.

Figure 10:
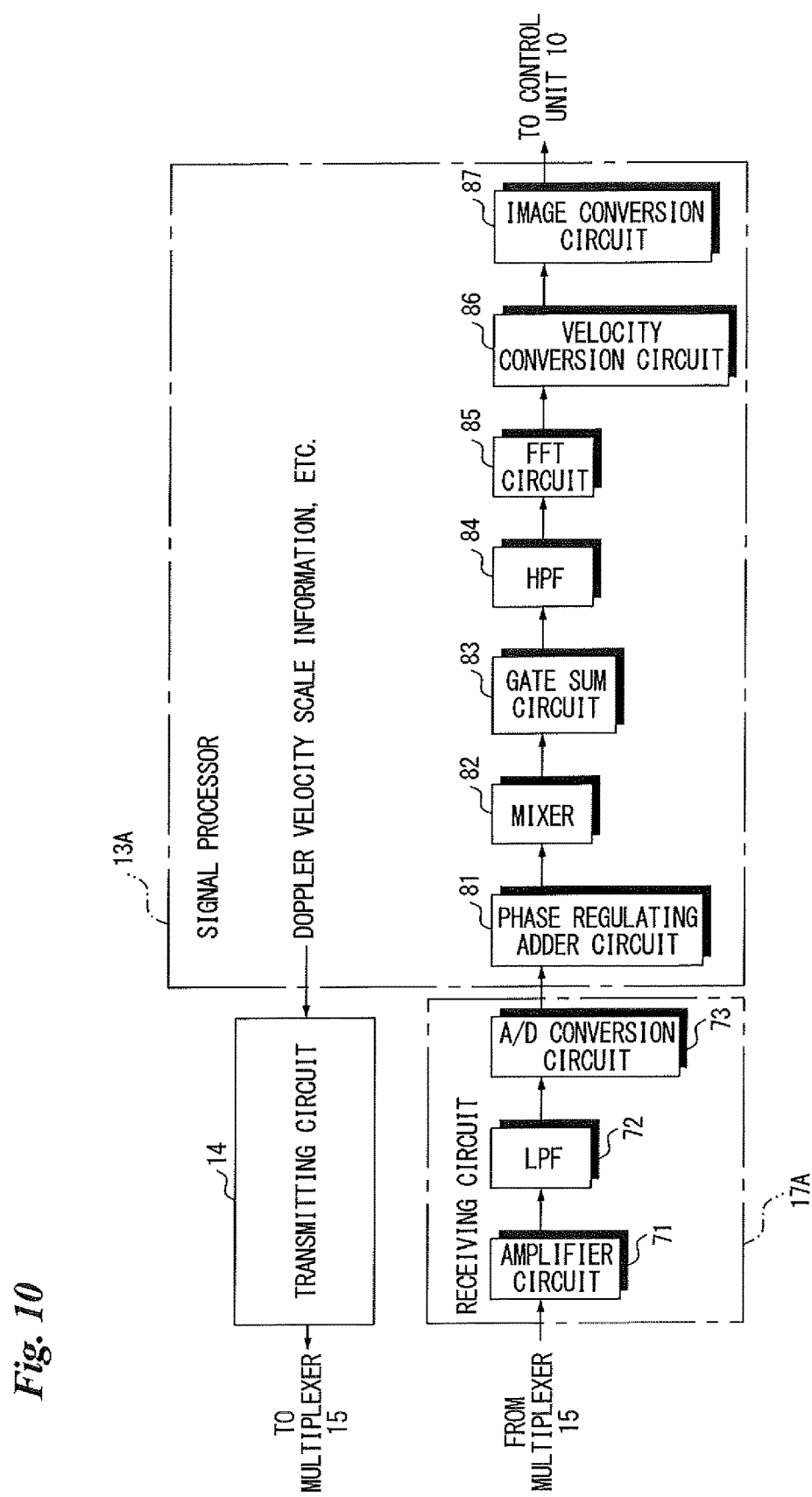
FIG. 10 is a block diagram illustrating the electrical configurations of a signal processor and receiving circuit.
Figure 11:
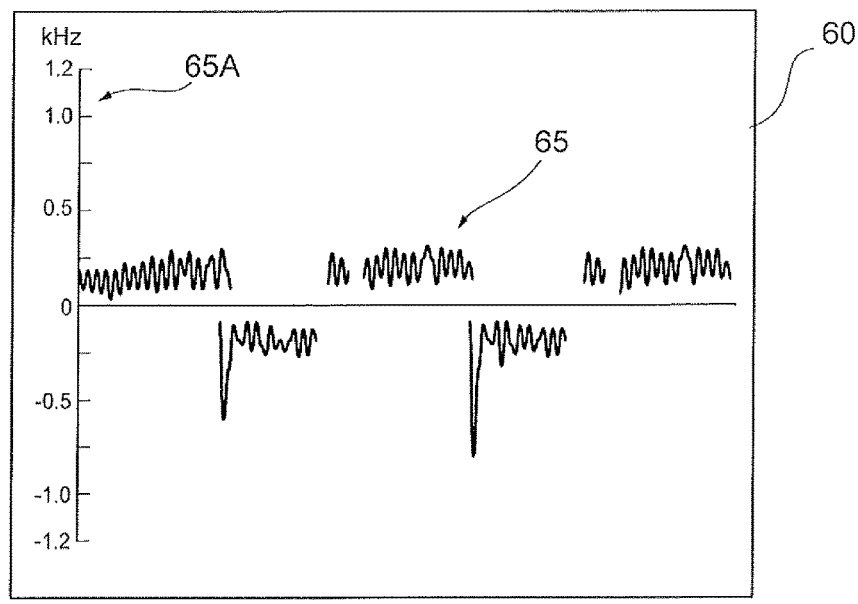
FIGS. 11 and 12 are examples of display screens of an ultrasound diagnostic apparatus.
Figure 12:
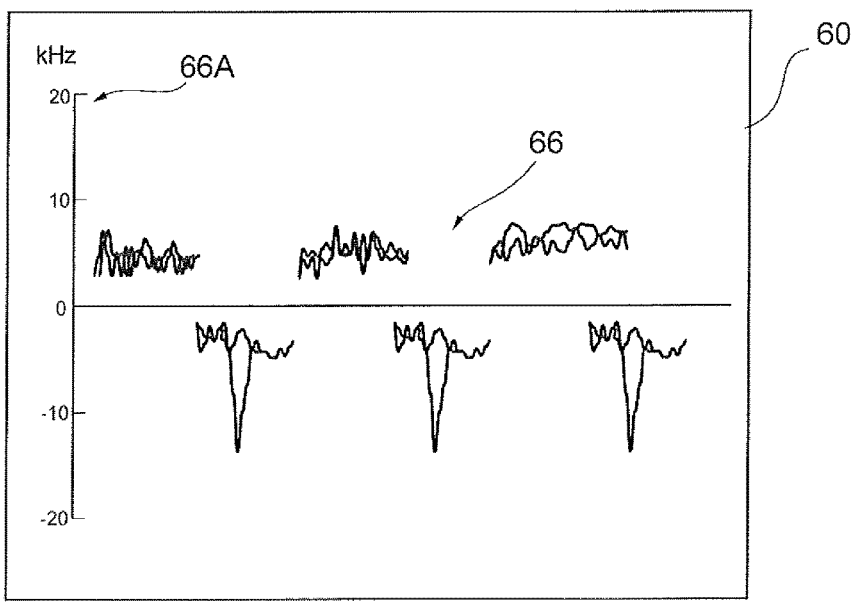

FIGS. 10 to 12 illustrate another embodiment of the present invention.

FIG. 10 is a block diagram illustrating the electrical configurations of a portion of a signal processor 13A, the transmitting circuit 14 and a receiving circuit 17A used in the ultrasound diagnostic apparatus. This arrangement is utilized in an ultrasound diagnostic apparatus (a so-called pulsed Doppler ultrasound diagnostic apparatus) that transmits pulsed ultrasound waves at regular intervals. In the ultrasound diagnostic apparatus shown in FIG. 1, the signal processor 13A shown in FIG. 10 is utilized instead of the signal processor 13 and, similarly, the receiving circuit 17A shown in FIG. 10 is utilized instead of the receiving circuit 17.

Data indicating the Doppler velocity scale set using the operating unit 12 is supplied from the signal processor 13A to the transmitting circuit 14. The ultrasound probe 16 is controlled in such a manner that the transmitting circuit 14 will transmit ultrasonic pulses at a repetition frequency that is twice the frequency of the boundary value of the Doppler velocity scale that has been set. A pulsed Doppler ultrasound diagnostic apparatus is such that even in a case where the velocity scale has been moved downward (and similarly, even if it has been moved upward), the waveform that was being displayed in the portion lower than the baseline (the 0-kHz reference line) owing to aliasing is just displayed in the upper portion. Therefore, the frequency of the boundary value that has been set by the user appears as is as the velocity scale.

The ultrasound echo signal obtained based upon the ultrasound echo from the specimen is amplified by an amplifier circuit 71 in the receiving circuit 17A and high-frequency components are removed by a low-pass filter 72 to perform anti-aliasing prior to an analog-to-digital conversion. The output signal of the low-pass filter 72 is converted to digital ultrasound echo data in an analog-to-digital conversion circuit 73. The output data of the analog-to-digital conversion circuit 73 is the output of the receiving circuit 17A and is input to the signal processor 13A.

The ultrasound echo data output from the receiving circuit 17A is input to a phase regulating adder circuit 81 in the signal processor 13A, undergoes phase-regulated addition and is detected in a mixer 82. Furthermore, a gate sum circuit 83 averages the real data and averages the imaginary data of a baseband signal within the sampling gate of the ultrasound diagnostic apparatus. Output data from the gate sum circuit 83 is applied to a high-pass filter 84 which, in a manner similar to that of the above-described high-pass filter 43 (see FIG. 2), removes low-frequency components from the entered data. The Doppler shift frequency is converted to a velocity scale in a fast-Fourier transform circuit 85. Output data from a velocity conversion circuit 86 is applied to an image conversion circuit 87 where it is converted to a luminance commensurate with the power of the moving body being measured. The output data from the image conversion circuit 86 is the output signal of the signal processor 13A and is applied to the control unit 10. The driver 19 is controlled by the control unit 10 and a waveform representing the velocity of the moving body is displayed on the liquid crystal panel 20. Further, control pulses for pulse-width control are applied to the driver 21 of the backlight 22 from the pulse-width controller 11 of the control unit 10. The backlight 22 illuminates the liquid crystal panel 20 with a brightness conforming to the duty ratio of the control pulses.

FIG. 11 is an example of a waveform 65 displayed on the display screen 60 of the liquid crystal panel 20.

A velocity scale 65A set using the operating unit 12 is being displayed on the left side of the display screen 60. In the case of an ultrasound diagnostic apparatus that transmits pulsed ultrasound waves at regular time intervals, often the velocity of a comparatively slow moving body is measured. Therefore, unlike the case of the ultrasound diagnostic apparatus of FIG. 2 that transmits ultrasound waves continuously, a boundary value of comparatively low value is set in such a manner that the velocity of a comparatively slow moving object can be observed. FIG. 11 illustrates the state of the velocity scale 65A in a case where 1.2 kHz (first boundary value), which is a boundary value lower than the boundary value (2.3 kHz) of the velocity scale shown in FIG. 5, has been set by the user. Since the set boundary value is less than 18 kHz, which is the threshold value, the pulse frequency for pulse-width control is set to 20 kHz (the first frequency) by the pulse-width controller 11 (frequency setting device). Since the frequency (20 kHz) of the pulses for pulse-width control is higher than the boundary value (1.2 kHz) of the velocity scale, noise produced from the pulses for pulse-width control does not appear on the display screen 60, as set forth above.

FIG. 12 is an example of a waveform 65 displayed on the display screen 60 of the liquid crystal panel 20.

A velocity scale 66A set using the operating unit 12 is being displayed on the left side of the display screen 60. In FIG. 12, 20 kHz (second boundary value), which is a boundary value having a frequency higher than the boundary value (1.2 kHz) of the velocity scale shown in FIG. 11, has been set. Since the set boundary value is greater than 18 kHz, which is the threshold value, the pulse frequency for pulse-width control is set to 200 kHz by the pulse-width controller 11 (frequency setting device). Since the frequency (200 kHz) of the pulses for pulse-width control is very much lower than the boundary value (20 kHz) of the velocity scale, even if noise produced from the pulses for pulse-width control appears on the display screen 60, it will not be superimposed upon the waveform 66 and the waveform will not be affected by the noise, as set forth above.

It will understood that, even if the velocity scales 65A and 66A shown in FIGS. 11 and 12 are moved up or down to broaden the range of frequencies that can be displayed, as shown in FIGS. 6 and 8, noise produced by the pulses used in pulse-width control will not influence the waveform 65 or 66, as described above with reference to FIGS. 6 and 8.

In the case of an ultrasound diagnostic apparatus that transmits pulsed ultrasound waves at regular time intervals, the velocity of the moving body undergoing measurement is comparatively low and, hence, the frequency of the boundary value that will be set is also comparatively low. This means that the threshold value for changing over the pulse frequency for pulse-width control may be made lower than the threshold value used in an ultrasound diagnostic apparatus that transmits ultrasound waves continuously.

Figure 13:
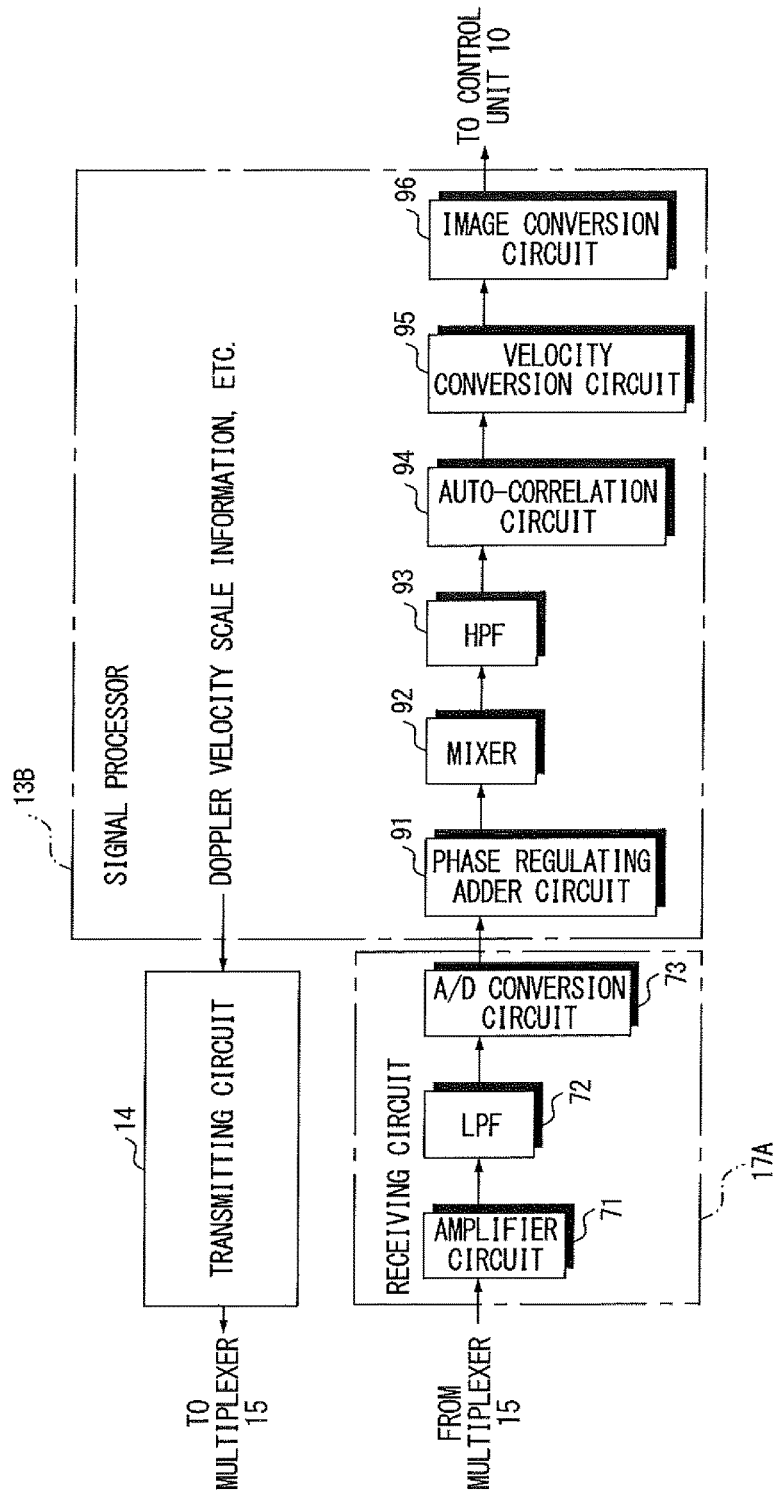
FIG. 13 is a block diagram illustrating the electrical configurations of a signal processor and receiving circuit.
Figure 14:
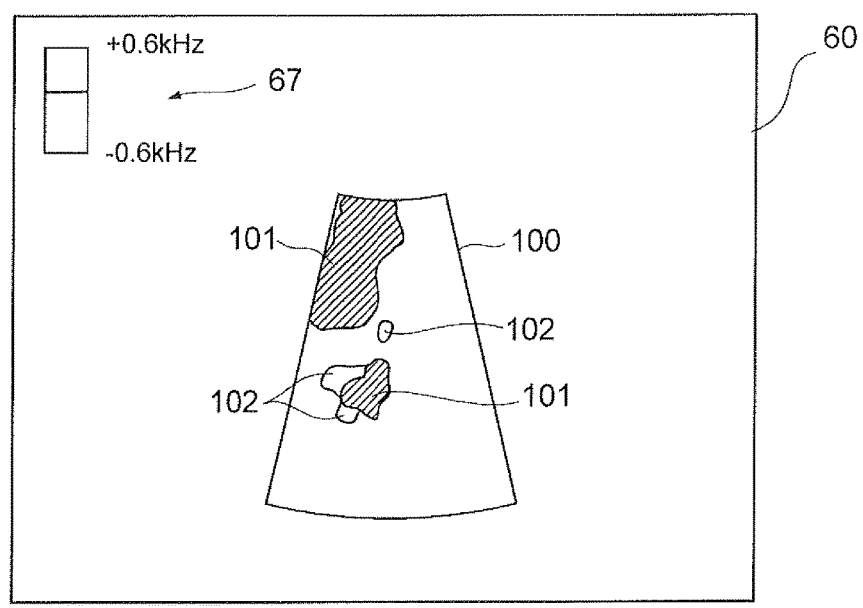
FIG. 14 is an example of a display screen of an ultrasound diagnostic apparatus.

FIGS. 13 and 14 illustrate a further embodiment of the present invention.

FIG. 13 relates to an ultrasound diagnostic apparatus (a so-called color Doppler ultrasound diagnostic apparatus) in which pulsed ultrasound waves are transmitted from an ultrasound probe at regular intervals and information representing the velocity of a moving body in the form of a difference in color is displayed on the liquid crystal panel (display unit) 20.

A signal processor 13B shown in FIG. 13 is utilized instead of the signal processor 13 of the ultrasound diagnostic apparatus shown in FIG. 1, and the receiving circuit 17A shown in FIG. 13 is utilized instead of the receiving circuit 17 illustrated in FIG. 1.

The transmitting circuit 14 is controlled by the control unit 10 in such a manner that the ultrasound probe 16 will transmit pulsed ultrasound waves at a repetition frequency that is twice the boundary value set using the operating unit 12.

An ultrasound echo signal that has been output from the multiplexer 15 is input to the signal processor 13B upon undergoing amplification in the amplifier circuit 71, removal of high-frequency components in the low-pass filter 72 and analog-to-digital conversion processing in the analog-to-digital conversion circuit 73, all of which take place in the receiving circuit 17A.

Ultrasound echo data (the ultrasound echo signal that has been converted to digital data) that has been input to the signal processor 13B is subjected to phase-regulated addition in a phase regulating adder circuit 91 and is detected in a mixer 92. Data that has been output from the mixer 92 has low-frequency components removed by a high-pass filter 93 in a manner similar to that performed by the high-pass filter 43 (see FIG. 2). The output data of the high-pass filter 93 is input to an auto-correlation circuit 94, which obtains the phase difference between pulses by auto-correlation processing. A velocity conversion circuit 95 finds the velocity of the moving body on the basis of the phase difference. Velocity v of the moving body is obtained from the equation v=(c/2)×Δθ(2π·T/fs), where c represents the speed of sound within the specimen, Δθ the phase difference, T the pulse repetition time, and fs the detected frequency. The calculated velocity is converted to color in the velocity conversion circuit 86. Output data from the velocity conversion circuit 86 is the output of the signal processor 13B and this signal is input to the control unit 10. The driver 19 is controlled by the control unit 10 and an image in which the velocity of the moving body is represented by color is displayed on the liquid crystal panel 20.

FIG. 14 is an example of an image displayed on the display screen 60 of the liquid crystal panel 20.

Velocity of a moving body measured within a region 100 of interest on the display screen 60 is displayed in color. For example, areas 101 indicated by hatching are blue in color and areas 102 that are not hatched are red in color. The blue areas 101 indicate the manner in which moving bodies move in a direction toward the ultrasound probe 16 and the red areas 102 indicate the manner in which moving bodies move in a direction away from the ultrasound probe 16. A velocity scale 67 is being displayed at the upper-left corner of the display screen 60. The boundary value has been set to 0.6 kHz by the user. Even in a case where the displayable velocity range has been moved downward (or upward), if velocity is displayed in color, as illustrated in FIG. 14, then the color representing the velocity of the moving body is merely displayed upon being changed. The frequency of the boundary value set by the user therefore appears as is as the velocity scale.

Thus, in a case where velocity of a moving body is represented by color, there are instances where the entire region 100 of interest takes on color such as by turning blue or red owing to noise ascribable to the pulse frequency of pulse-width control, as mentioned above, and it may appear that the entire region 100 of interest is moving at low speed. In this embodiment, as described above, in a case where the pulse frequency of pulse-width control is less than the threshold value, the pulse frequency rises and therefore falls outside the range of color that can be displayed by the velocity scale, and in a case where the pulse frequency of pulse-width control is equal to or greater than the threshold value, the pulse frequency declines. In a case where the frequency that can be displayed by the velocity scale is set to a high range, low-frequency noise will not appear as color. This makes it possible to avoid misdiagnosis.

Figure 15:
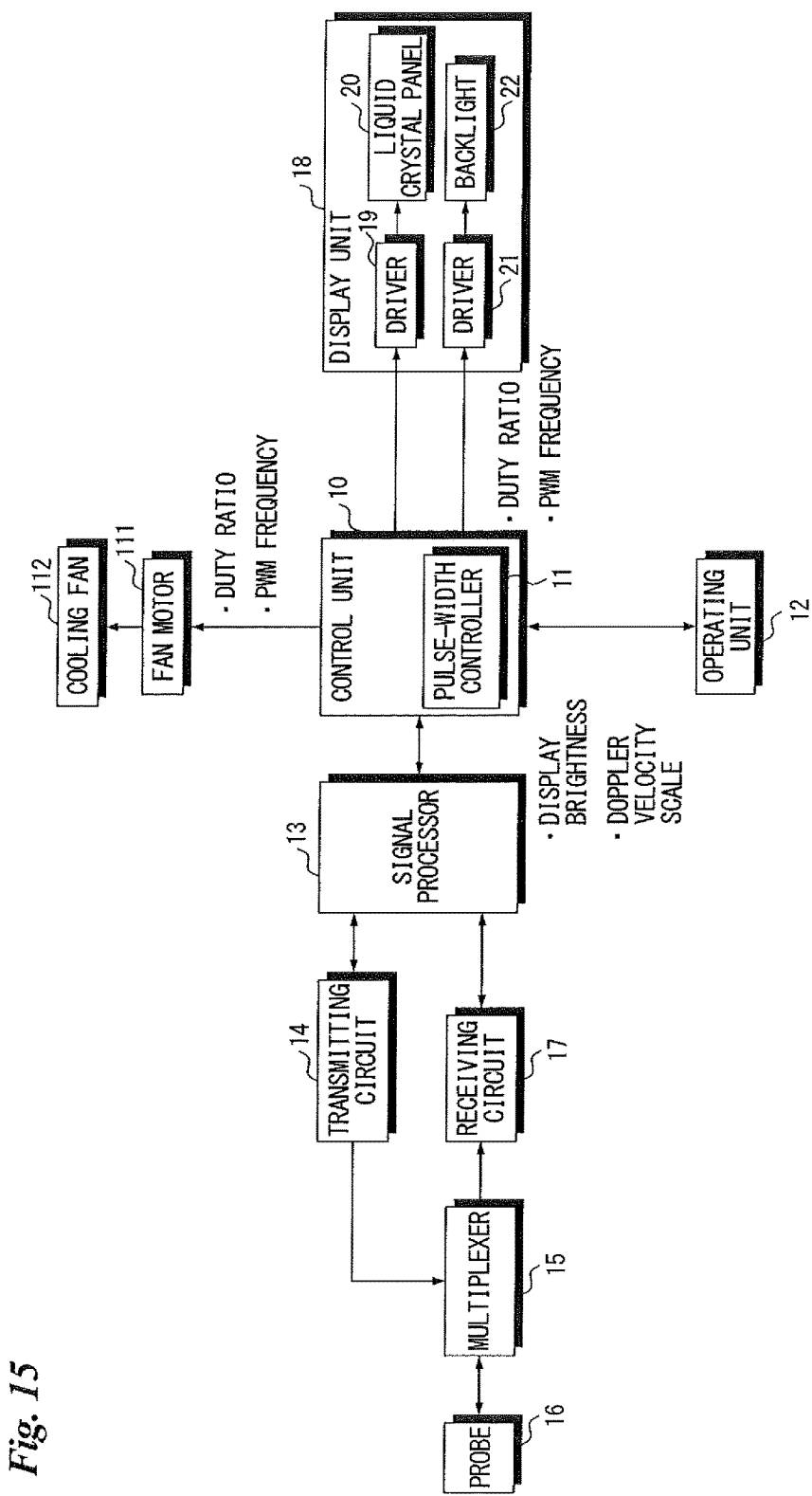
FIG. 15 is a block diagram illustrating the electrical configuration of an ultrasound diagnostic apparatus.
Figure 16:
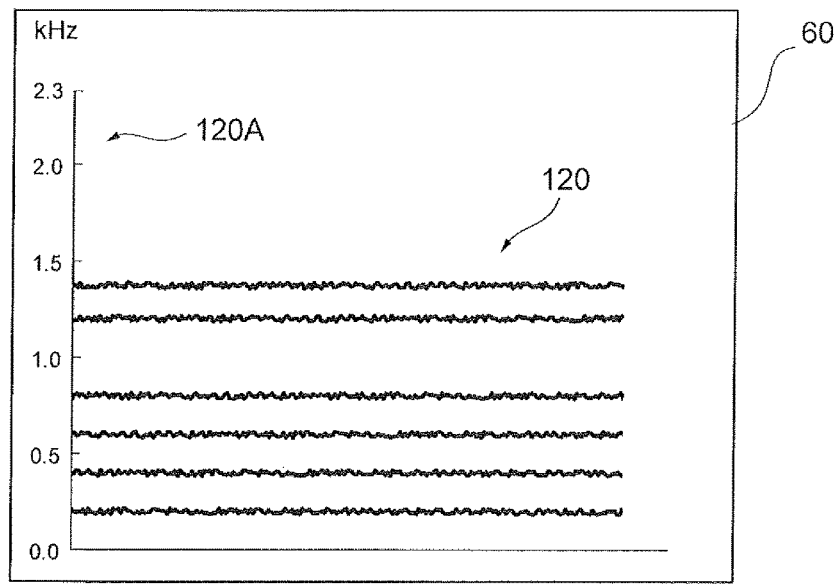
FIGS. 16 and 17 are examples of display screens of an ultrasound diagnostic apparatus according to the prior art.
Figure 17:
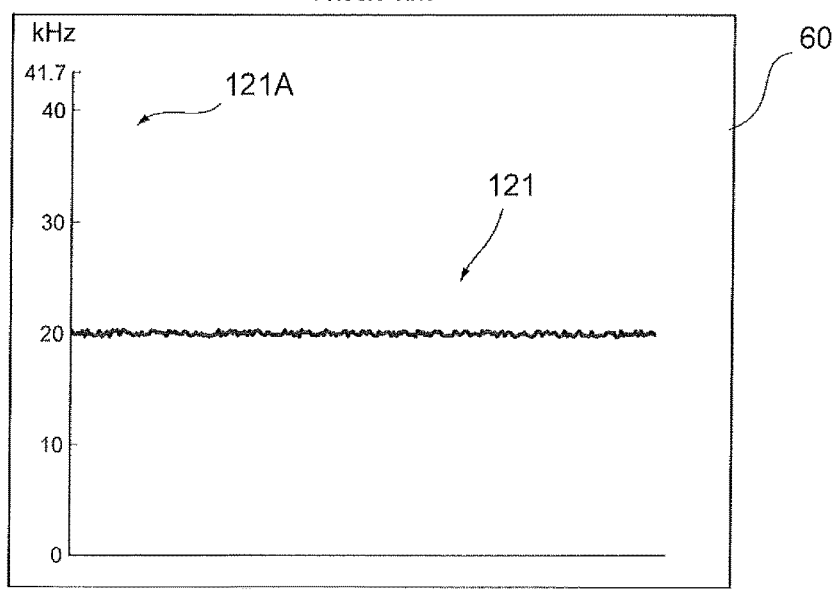

FIG. 15, which illustrates yet another embodiment, is a block diagram illustrating the electrical configuration of an ultrasound diagnostic apparatus. Components in FIG. 15 identical with those shown in FIG. 1 are designated by like reference characters and need not be described again.

The ultrasound diagnostic apparatus shown in FIG. 15 is provided with a cooling fan 112. A fan motor 111 that controls the amount of rotation of the cooling fan 112 is pulse-width controlled. Pulses for pulse-width control are applied to the fan motor 111 by the pulse-width controller 11 of the control unit 10, whereby the fan motor 111 is subjected to pulse-width control. The cooling fan 112 has a function for cooling at least one of the signal processor 13 (velocity calculation device), control unit 10 (display control device) and pulse-width controller 11 (frequency setting device). Preferably, the cooling fan 112 cools the signal processor 13. The reason for this is that a large amount of computation is required in the signal processor 13 in order to calculate the velocity of a moving body within a specimen using the ultrasound echo data.

In a case where the fan motor 111 is controlled by pulse-width control, in a manner similar to the case where brightness of the backlight 22 is controlled by pulse-width control, it may be arranged so that the pulse frequency of pulse-width control is changed in accordance with the size of the boundary value set using the operating unit 12 as described above. As mentioned above, if the boundary value set using the operating unit 12 is less than 18 kHz, which is the threshold value, the pulse frequency for controlling the fan motor 111 is set to 20 kHz. If the boundary value set using the operating unit 12 is equal to or greater than 18 kHz, which is the threshold value, the pulse frequency for controlling the fan motor 111 is set to 200 Hz. It will be understood that, by adopting this arrangement, noise ascribable to the pulses that control the fan motor 111 will not affect the waveform and color, etc., that represent the velocity of the moving body.

In the foregoing embodiments, two types of velocity scale are switched between in each ultrasound diagnostic apparatus. However, an arrangement may be adopted in which not two types but many more types (ten, for example) of velocity scale are switched among in accordance with the set boundary value. In such an ultrasound diagnostic apparatus as well, the frequency of pulses for pulse-width control is changed over, in the manner described above, in dependence upon whether the set boundary value is less than the threshold value or equal to or greater than the threshold value. Furthermore, the liquid crystal panel 20 may be provided with a touch-sensitive panel. If a touch-sensitive panel is provided, the setting of a velocity scale conforming to the setting of the boundary value can be performed using the touch-sensitive panel or the operating unit 12. Moving of the velocity scale can be controlled using the touch-sensitive panel. Furthermore, rather than setting the velocity scale using the operating unit 12, an arrangement may be adopted in which the velocity scale is changed over automatically using the control unit 10 in accordance with the measured velocity of the moving body in such a manner that the velocity of the moving body will be displayed over a range equal to or greater than half of the range of the velocity scale. In such case the control unit 10 that changes over and sets the velocity scale will function as a velocity scale setting device, onward is repeated.

As many apparently widely different embodiments of the present invention can be made without departing from the spirit and scope thereof, it is to be understood that the invention is not limited to the specific embodiments thereof except as defined in the appended claims.

What is claimed is:

1. An acoustic wave diagnostic apparatus comprising:
    an acoustic probe for transmitting acoustic waves toward a specimen and outputting an acoustic echo signal representing an acoustic echo from the specimen;
    a velocity scale setting device for setting a velocity scale having a boundary value, the velocity scale being used to display a velocity of a moving body within the specimen;
    a velocity calculation device for calculating the velocity of the moving body within the specimen using the acoustic echo signal output from said acoustic probe;
    a display control device for displaying information, which indicates the calculated velocity of the moving body, on a display unit in accordance with the velocity scale set by said velocity scale setting device;
a brightness control device for creating pulses used in backlight control, the brightness of the display unit being adjusted by a backlight; and
a frequency setting device for setting the frequency of the pulses based on the set velocity scale for displaying the calculated velocity of the moving body, the frequency setting device configured to
if the velocity scale set by the user has a first boundary value which is less than a threshold value, set the frequency of the pulses for controlling the brightness of the display to a first frequency which is equal to or greater than the first boundary value, and
if the velocity scale set by the user has a second boundary value which is equal to or greater than the threshold value, set the frequency of the pulses for controlling the brightness of the display to a second frequency which is lower than any of the first frequency and the frequency corresponding to the first boundary value which is less than a threshold value.

2. An acoustic wave diagnostic apparatus comprising:
an acoustic probe for transmitting acoustic waves toward a specimen and outputting an acoustic echo signal representing an acoustic echo from the specimen;
a velocity scale setting device for setting a velocity scale having a boundary value set by a user, the velocity scale being used to display a velocity of a moving body within the specimen;
a velocity calculation device for calculating the velocity of the moving body within the specimen using the acoustic echo signal output from said acoustic probe;
a display control device for displaying information, which indicates the calculated velocity of the moving body, on a display unit in accordance with the velocity scale set by said velocity scale setting device;
a cooling fan for cooling at least one of said velocity calculation device and display control device;
a fan motor for controlling rotation of said cooling fan; and
a frequency setting device for setting the frequency of pulses used in said fan motor based on the set velocity scale, the frequency setting device configured to
if the velocity scale set by the user has a first boundary value which is less than a threshold value, set the frequency of the pulses used in said fan motor to a first frequency which is equal to or greater than the first boundary value, and
if the velocity scale set by the user has a second boundary value which is equal to or greater than the threshold, set the frequency of pulses used in said fan motor to a second frequency which is lower than any of the first frequency and the frequency corresponding to the first boundary value which is less than a threshold value.

3. The apparatus according to claim 1, further comprising a high-pass filter, which has a cut-off frequency equal to or greater than the second frequency, for eliminating low-frequency components of the acoustic echo signal that is output from said acoustic probe.

4. The apparatus according to claim 1, wherein duty ratio of pulses at the first frequency and duty ratio of pulses at the second frequency are identical.

5. The apparatus according to claim 1, wherein
said acoustic probe transmits continuous waves of the acoustic waves; and
said display control device displays a waveform, which indicates the velocity of a moving body within the specimen, on the display unit.

6. The apparatus according to claim 5, further comprising a low-pass filter for eliminating high-frequency components, at a cut-off frequency equal to or greater than a frequency corresponding to the velocity of the boundary value, from the acoustic echo signal that is output from the acoustic probe, in a case where a velocity scale that includes the boundary value has been set by said velocity scale setting device.

7. The apparatus according to claim 1, wherein
said acoustic probe transmits pulsed acoustic waves at regular intervals; and
said display control device displays a waveform, which indicates the velocity of a moving body within the specimen, on the display unit.

8. The apparatus according to claim 1, wherein
said acoustic probe transmits pulsed acoustic waves at regular intervals; and
said display control device is a color Doppler display control device for displaying information, which represents the velocity of a moving body within the specimen as a difference in color, on the display unit.

9. A method of controlling an acoustic wave diagnostic apparatus, comprising steps of:
an acoustic probe transmitting acoustic waves toward a specimen and outputting an acoustic echo signal representing an acoustic echo from the specimen;
a velocity scale setting device setting a velocity scale having a boundary value set by a user, the velocity scale being used to display a velocity of a moving body within the specimen;
a velocity calculation device calculating the velocity of the moving body within the specimen using the acoustic echo signal output from the acoustic probe;
a display control device displaying information, which indicates the calculated velocity of the moving body, on a display unit in accordance with the velocity scale set by the velocity scale setting device;
a brightness control device for creating pulses used in backlight control, the brightness of the display unit being adjusted by a backlight; and
a frequency setting device setting the frequency of the pulses based on the set velocity scale for displaying the calculated velocity of the moving body, the frequency setting device configured to
if the velocity scale set by the user has a first boundary value which is less than a threshold value, set the frequency of the pulses for controlling the brightness of the display to a first frequency which is equal to or greater than the first boundary value, and
if the velocity scale set by the user has a second boundary value which is equal to or greater than the threshold value, set the frequency of pulses for controlling the brightness of the display to a second frequency which is lower than any of the first frequency and the frequency corresponding to the first boundary value which is less than a threshold value.

10. A method of controlling an acoustic wave diagnostic apparatus, comprising steps of:
an acoustic probe transmitting acoustic waves toward a specimen and outputting an acoustic echo signal representing an acoustic echo from the specimen;

a velocity scale setting device setting a velocity scale having a boundary value set by a user, the velocity scale being used to display a velocity of a moving body within the specimen;

a velocity calculation device calculating the velocity of the moving body within the specimen using the acoustic echo signal output from the acoustic probe;

a display control device displaying information, which indicates the calculated velocity of the moving body, on a display unit in accordance with the velocity scale set by the velocity scale setting device;

a cooling fan cooling at least one of the velocity calculation device and display control device;

a fan motor controlling rotation of the cooling fan; and a frequency setting device setting the frequency of pulses used in the fan motor based on the set velocity scale, the frequency setting device configured to if the velocity scale set by velocity scale set by the user has a first boundary value which is less than a threshold value, set the frequency of the pulses used in the fan motor to a first frequency which is equal to or greater than the first boundary value, and if the velocity scale set by the user has a second boundary value which is equal to or greater than the threshold value, set the frequency of the pulses used in the fan motor to a second frequency which is lower than any of the first frequency and the frequency corresponding to the first boundary value which is less than a threshold value.

* * * * *